(12) United States Patent
Hillers et al.

(10) Patent No.: US 8,911,715 B2
(45) Date of Patent: Dec. 16, 2014

(54) L-MENTHYL-N-(2-HYDROXYPHENYL) CARBAMATE

(75) Inventors: Stephan Hillers, Holzminden (DE); Heiko Oertling, Holzminden (DE); Claudia Goemann, Warbsen (DE)

(73) Assignee: Symrise AG, Holzminden (DE)

( * ) Notice: Subject to any disclaimer, the term of this patent is extended or adjusted under 35 U.S.C. 154(b) by 0 days.

(21) Appl. No.: 12/994,085

(22) PCT Filed: May 25, 2009

(86) PCT No.: PCT/EP2009/056261
§ 371 (c)(1),
(2), (4) Date: Feb. 14, 2011

(87) PCT Pub. No.: WO2009/144179
PCT Pub. Date: Dec. 3, 2009

(65) Prior Publication Data
US 2011/0129432 A1    Jun. 2, 2011

Related U.S. Application Data

(60) Provisional application No. 61/057,527, filed on May 30, 2008.

(51) Int. Cl.
| A61K 8/00 | (2006.01) |
| A61Q 15/00 | (2006.01) |
| A61K 8/42 | (2006.01) |
| C07C 271/38 | (2006.01) |
| A61Q 5/12 | (2006.01) |
| A61Q 19/00 | (2006.01) |
| A61Q 5/02 | (2006.01) |

(52) U.S. Cl.
CPC ......... *C07C 271/38* (2013.01); *A61K 2800/522* (2013.01); *A61Q 15/00* (2013.01); *A61Q 5/12* (2013.01); *C07C 2101/16* (2013.01); *A61K 8/42* (2013.01); *A61Q 19/00* (2013.01); *A61Q 5/02* (2013.01)
USPC ......................................................... 424/65

(58) Field of Classification Search
None
See application file for complete search history.

(56) References Cited

U.S. PATENT DOCUMENTS

| 4,091,090 A | 5/1978 | Sipos | |
| 4,136,163 A * | 1/1979 | Watson et al. | 424/54 |
| 5,795,616 A * | 8/1998 | Greenberg | 426/650 |
| 2002/0028224 A1 * | 3/2002 | Bajor et al. | 424/401 |
| 2004/0028714 A1 * | 2/2004 | Blondeau et al. | 424/405 |
| 2004/0253191 A1 * | 12/2004 | Maxwell et al. | 424/49 |
| 2006/0063764 A1 * | 3/2006 | Gautschi | 514/237.5 |
| 2007/0203148 A1 * | 8/2007 | Dunkel et al. | 514/252.05 |
| 2007/0280892 A1 * | 12/2007 | Kindel et al. | 424/49 |
| 2007/0293455 A1 * | 12/2007 | Dunkel et al. | 514/63 |
| 2008/0058389 A1 * | 3/2008 | Dunkel et al. | 514/354 |
| 2008/0107610 A1 * | 5/2008 | Maxwell et al. | 424/48 |
| 2012/0323198 A1 * | 12/2012 | Pesce et al. | 604/367 |

FOREIGN PATENT DOCUMENTS

| EP | 799174 A1 | 10/1997 |
| EP | 1269983 A1 | 1/2003 |
| WO | WO-0202071 A2 | 1/2002 |
| WO | WO-03024907 A1 | 3/2003 |
| WO | WO-2005004601 A1 | 1/2005 |

OTHER PUBLICATIONS

Barber, M. et al: "Antibacterial action of o-aminophenol," British Medical Journal, 1944, pp. 754-755, XP008110319.
Vieillefosse, et al., "Nouveaux anesthésiques locaux dans la série des uréthanes cyclaniques," *Annales Pharmaceutiques Francaises*, 1958, pp. 408-413.
Brandis, et al., : Lehrbuch der Medizinischen Mikrobiologie, 6th revised edition, Gustav Fischer Verlag Stuttgart, pp. 200-205, 1988 et seq.
Pellegrini, et al., "Antioxidant Activity Applying an Improved ABTS Radical Cation Decolorization Assay," Free Radical Biology & Medicine, vol. 26, Nos. 9/10, pp. 1231-1237, 1999.

* cited by examiner

*Primary Examiner* — Robert A Wax
*Assistant Examiner* — Olga V Tcherkasskaya
(74) *Attorney, Agent, or Firm* — Novak Druce Connolly Bove + Quigg LLP

(57) ABSTRACT

The present invention relates to the compound L-menthyl-N-(2-hydroxyphenyl)carbamate, which is effective against body perspiration odor bacteria, in particular against armpit perspiration odor bacteria, and simultaneously effective as an antioxidant, of the following formula, a method for the production thereof and its use.

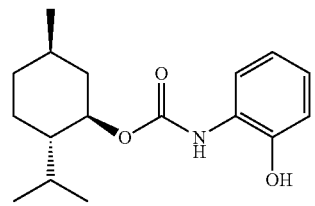

12 Claims, No Drawings

L-MENTHYL-N-(2-HYDROXYPHENYL) CARBAMATE

CROSS-REFERENCE TO RELATED APPLICATIONS

This application is a National Phase filing under 35 U.S.C. §371 of PCT/EP2009/056261, filed May 25, 2009, which claims priority to Provisional Patent Application No. 61/057,527, filed in the United States on May 30, 2008, the entire contents of which is incorporated herein by reference.

The present invention relates to the compound L-menthyl-N-(2-hydroxyphenyl)carbamate, which is effective against body perspiration odor bacteria, in particular against armpit perspiration odor bacteria, and simultaneously effective as an antioxidant, of the following formula, a method for the production thereof and its use.

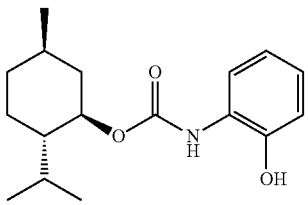 [SMILES: CC(C)[C@@H]1CC[C@@H](C)C[C@H]1OC(=O)Nc1ccccc1O]

The compound according to the invention is suitable as an active ingredient for treating microorganisms causing perspiration odor.

The human skin is colonized by a large number of various bacteria. Most of these bacteria are not pathogenic and irrelevant to the physiological state of the skin and to its odor. Others, on the other hand, can considerably influence the healthy state of the skin. Some microorganisms strongly influencing the human skin flora in conjunction with human perspiration odor are compiled in the following table.

| Microorganisms: | |
| --- | --- |
| Staphylococcus epidermidis | Armpit odor |
| Corynebacterium xerosis | Armpit odor |
| Brevibacterium epidermidis | Armpit odor, foot odor |

Unpleasantly smelling decomposition products, which can strongly influence physical wellbeing, are produced from more or less weakly smelling preliminary stages owing to the bacterial decomposition in the body's own materials contained in the perspiration, such as, for example, unsaturated fatty acids. To prevent the production of the substances responsible for the perspiration odor, products are used in cosmetics, which either prevent the formation of body perspiration (so-called antiperspirants) or substances which inhibit the growth of perspiration odor bacteria, in other words the bacteria of the human skin responsible for the odor formation (deodorants).

Types of bacteria such as *staphylococcus epidermidis*, *corynebacterium xerosis* and *brevibacterium epidermidis* are decisively responsible for the formation of perspiration odor, in particular armpit and foot odor and are therefore, in particular, designated as perspiration odor bacteria according to the invention. Therefore, there is a constant need in the cosmetics industry for new means for treating these and other microorganisms causing body odor (including armpit and foot odor).

"Treatment" is, in this case, taken to mean in the framework of the present text, any form of influence on the relevant microorganisms, in which the multiplication of these microorganisms is inhibited and/or the microorganisms are killed. The term "treatment" therefore includes cosmetic methods for controlling the number of bacteria on a surface, in particular an outer body surface, in particular the skin or hair, of a person, or of pieces of clothing touching an outer body surface of a person, including shoes.

In the search for corresponding means which are effective against body perspiration odor bacteria it has to be taken into account here that the substances used in cosmetic and/or pharmaceutical products should be
- toxicologically harmless,
- very compatible with the skin,
- stable (in particular in the usual cosmetic and/or pharmaceutical formulations),
- preferably odorless,
- economically producible (i.e. using standard methods and/or proceeding from standard precursors).

The search for suitable (active) substances, which have one or more of said properties to an adequate extent, is made more difficult for the person skilled in the art in that no clear dependency exists between the chemical structure of a substance, on the one hand, and its biological activity relative to certain microorganisms (germs).

It was therefore the object of the present invention to disclose a suitable active ingredient for use in cosmetic and/or pharmaceutical products, which is effective at least against a microorganism, preferably, however, against a plurality of the microorganisms discussed above, and thus preferably has further positive (preferably one or more of the above-mentioned) properties.

The object is achieved by disclosing the compound according to the invention L-menthyl-N-(2-hydroxyphenyl)carbamate. Furthermore, the use of L-menthyl-N-(2-hydroxyphenyl)carbamate is disclosed according to the invention for inhibiting and/or killing the bacteria (in particular the *staphylococcus*, *corynebacterium* and *brevibacterium* types) responsible for the formation of perspiration odor (including armpit and foot perspiration odor),
- cosmetic or therapeutic treatment of body perspiration odor bacteria,
- cosmetic or therapeutic control of the number of body perspiration odor bacteria on an outer body surface or a piece of clothing touching a body surface of this type during intended use, and/or
- production of a pharmaceutical preparation for changing or reducing body odor and/or for treating body perspiration odor bacteria.

In a preferred method for the cosmetic and/or therapeutic treatment of microorganisms causing perspiration odor, in particular armpit perspiration odor, an effective quantity of the L-menthyl-N-(2-hydroxyphenyl)carbamate is applied topically to the human body, so the growth and/or metabolism of the microorganism(s) optionally present can be inhibited and/or these can be killed.

The compound menthyl-N-(4-hydroxyphenyl)carbamate is described in *Annales Pharmaceutiques Francaises*, 1958, 408 in an investigation about local anesthetics. Nothing is reported about the effectiveness of this substance for combating body perspiration odor and the aforementioned organisms responsible for perspiration odor.

A structurally similar compound namely menthyl-N-[(2-hydroxy-6-methyl)-phenyl]carbamate, was described in WO 02/002071 as a sebum-controlling active ingredient in cosmetic applications.

The compound according to the invention has a strong antimicrobial action with respect to perspiration odor bacteria, in other words odor-forming microorganisms of the human skin, and thus can be excellently used as an alternative or as a supplement to known antimicrobial active ingredients (such as, for example, farnesol) in cosmetic products and the like as a deodorant.

The use concentration of the compound according to the invention in a cosmetic end product, in other words in a preparation intended directly for topical application on a human body (for example a deodorant, an antiperspirant or a shampoo) is preferably in the range of 0.001 to 20% by weight, preferably in the range of 0.05 to 5% by weight, more preferably in the range of 0.1 to 3% by weight, in each case based on the total mass of the cosmetic product.

The preparation according to the invention is preferably present in a cosmetic end product, in a roll-on deodorant, aerosol spray device (with or without propellant) or non-aerosol spray device (with or without propellant).

A particularly preferred preparation according to the invention (as described above) is a deodorant or antiperspirant for application on the human body. A preparation according to the invention preferably contains (depending on the desired mode of action) one or more of the following active ingredients:

(1) Antimicrobially effective substances, which inhibit the development of the microorganisms responsible for body perspiration odor; for example 2-phenoxyethanol, farnesol, glycerol esters and glycerol ethers such as glycerol monolaurate, glycerol monocaprinate, hexoxyglycerol, octoxyglycerol (=ethylhexylglycerol, 3-(2-ethylhexyloxy-1,2-propane diol) or Sensiva® SC 50 (from Schülke & Mayr), aliphatic 1,2-diols such as, for example 1,2-decane diol (EP 1 269 983), araliphatic alcohols such as, for example, described in EP 799 174, preferably 4-methyl-4-phenyl-2-pentanol (Vetikol; WO 03/024907) or 2-methyl-4-phenyl-2-butanol (1,1-dimethyl-3-phenylpropanol, alpha,alpha-dimethylphenethylcarbinol), 2-benzylheptane-1-ol (Jasmol; 2-n-pentyl-3-phenylpropane-1-ol), 2,2-dimethyl-3-phenylpropanol (muguet alcohol; cf. U.S. Pat. No. 4,091,090), antimicrobially effective secondary alcohol, such as for example described in WO 2005/004601, in particular 3-methyl-6-phenyl-2-hexanol, dimethylphenyl)-2-butanol, 6-(4-isopropylphenyl)-3-methyl-2-hexanol, 4-(2,4,5-trimethylphenyl)-2-butanol, 3,3-dimethyl-4-phenyl-2-butanol, 3-methyl-4-(2-methylphenyl)-2-butanol, dimethylphenyl)-2-hexanol, aliphatic carboxylic acids such as 2-hexyloctanoic acid, 2-hexyldecanoic acid, 2-butyloctanoic acid or 2-butyldecanoic acid;

(2) enzyme-inhibiting substances, which prevent the action of enzymes, which are involved in the formation of perspiration odor; in particular citric acid esters and metal-chelating substances such as EDTA (ethylene diamine tetracetic acid), EGTA (ethylene glycol tetracetic acid) and DTPA (diethylene triamine pentacetic acid, pentetic acid);

(3) odor-absorbing substances, which absorb the substances responsible for the perspiration odor; for example zinc ricinoleate, cyclodextrine;

(4) antiperspirants, which inhibit the perspiration secretion and therefore remove the culture medium from the bacteria responsible for the perspiration odor. Astringent metal salts are preferably used in general as antiperspirants, particularly inorganic and organic metal salts of the elements aluminum, zinc, magnesium, tin and zircon and mixtures thereof, halogenides, such as aluminum chloride, basic aluminum hydroxychlorides, zirconyl oxychlorides and zirconyl hydroxychlorides and mixtures thereof in particular being used. These aluminum and zirconium salts and mixtures thereof are frequently also used in a complexed form, propylene glycol, polyethylene glycol, or glycine preferably being used as the complexing agent.

According to the invention, a production method is also disclosed for producing L-menthyl-N-(2-hydroxyphenyl)carbamate by reacting chloroformic acid menthyl ester with ortho-hydroxyaniline in the presence of a base.

The base is preferably an amine, more preferably a tertiary amine such as pyridine, tributylamine or triethylamine.

It has proven to be particularly advantageous for the compound L-menthyl-N-(2-hydroxyphenyl)carbamate according to the invention to have only a weak odor of its own or even be completely odorless. This property predestines it for use in perfume compositions or perfumed articles, in particular cosmetic preparations, as the original odor profile of the perfume composition or the perfumed article is not changed by the presence of the compound according to the invention.

The invention also relates to preparations, which in addition to (a) a quantity of L-menthyl-N-(2-hydroxyphenyl)carbamate which is antimicrobially effective against body perspiration odor bacteria, also comprises (b) one or more carrier substances compatible with component (a).

Preferred carrier substances here are selected from the group consisting of ethanol, isopropanol, diethylene glycol monoethylether, glycerol 1,2-propylene glycol, 1,2-butylene glycol, 1,3-butylene glycol, 1,2-pentane diol, 1,5-pentane diol, 1,2-hexane diol, 1,6-hexane diol, 1,2-octane diol, dipropylene glycol, diethyl phthalate, triethyl citrate, isopropyl myristate, triacetine, plant oils, (for example, sunflower oil, coconut oil, palm oil, olive oil, *macadamia* nut oil, rapeseed oil, (hydrogenated) castor oil), silicone oils (in particular dimethicones, cyclomethicones), fats, waxes (in particular beeswax), mineral oil, sodium stearate, sodium palmitate and mixtures thereof.

Particularly preferred carrier substances are selected from the group consisting of ethanol, glycerol, 1,2-propylene glycol, 1,2-butylene glycol, 1,3-butylene glycol, 1,2-pentane diol, dipropylene glycol, triethyl citrate, isopropyl myristate, plant oils, silicone oils, fats and/or waxes.

Surprisingly it has also been shown that the compound according to the invention has the above-described properties against body perspiration odor bacteria with a simultaneous antioxidant effect.

Oxidative damage in biological systems is caused and promoted by many different factors. Antioxidants do not only play a decisive role in disease prophylaxis, but also slow down ageing processes in the human skin, in that they prevent the oxidative decomposition of individual cell components by reactive oxygen species.

In cosmetics or in topical pharmaceutical applications, it is therefore sometimes advantageous to also incorporate antioxidants in the corresponding formulation for topical applications such as skin and/or hair in order to thus bring about protection in advance from extrinsically or intrinsically produced reactive oxygen.

Moreover, antioxidants have a protective influence on instable or sensitive chemicals and formulation constituents, which can be oxidized very easily and therefore prolong the life and increase the storage stability of a formulation of this type. For these reasons, synthetic and also natural antioxidants are widely used in the most varied cosmetic or pharmaceutical products.

Further aspects of the present invention emerge from the accompanying claims and the following examples, without, however, restricting these. If not otherwise stated, all the details relate to the weight.

1. SYNTHESIS OF L-MENTHYL-N-(2-HYDROXYPHENYL) CARBAMATE 500 g 2-hydroxyaniline are prepared in 800 ml toluene in a three-necked flask with a head stirrer and thermometer. A solution of 435 g pyridine in 300 ml toluene is added within 5 minutes at room temperature. 1,090 g of a solution of menthyl chloroformate in toluene are added at 0° C. within 3 hours and re-stirred for an hour at room temperature. The precipitated precipitate is filtered off, washed with 500 ml toluene and discarded. The organic phase is washed at room temperature with 1,000 ml water, the washing water is re-extracted with 250 ml toluene in each case and the purified organic phases are dried. After removal of the solvent, 1,146 g of crude product are obtained which is recrystallized from 1,030 g n-heptane. 538 g L-menthyl-N-(2-hydroxyphenyl) carbamate is thus obtained as white solid.

$^1$H-NMR (400 MHz, CDCl$_3$, TMS): L=0.81-0.94 (m, 1H), 0.82 (d, J=7.0 Hz, 3H), 0.92 (d, J=7.0 Hz, 3H), 0.93 (d, J=6.6 Hz, 3H), 1.00-1.16 (m, 2H), 1.35-1.44 (m, 1H), 1.45-1.58 (m, 1H), 1.67-1.74 (m, 2H), 1.97 (dhept., J=2.6 Hz, J=7.0 Hz, 1H), 2.08-2.12 (m, 1H), 4.68 (dt, J=4.4 Hz, J=10.9 Hz, 1H), 6.71 (s, br., 1H), 6.87 (ddd, J=1.6 Hz, J=7.3 Hz, J=7.9 Hz, 1H), 6.97 (dd, J=1.5 Hz, J=8.1 Hz, 1H), 7.05 (ddd, J=1.6 Hz, J=7.3 Hz, J=8.1 Hz, 1H), 7.11 (dd, J=1.5 Hz, J=8.0 Hz, 1H), 7.90 (s, br., 1H) ppm.

$^{13}$C-NMR (400 MHz, CDCl$_3$, TMS): L=16.39 (CH$_3$), 20.78 (CH$_3$), 22.00 (CH$_3$), 23.45 (CHO, 26.29 (CH), 31.41 (CH), 34.17 (CH$_2$), 41.19 (CH$_2$), 47.31 (CH), 76.61 (CH), 118.77 (CH), 120.87 (CH), 121.28 (CH), 125.42 (C), 125.64 (CH), 147.29 (C), 155.39 (CO) ppm.

MS (EI): m/z=291 (12, [M$^+$]), 153 (100), 138 (7), 109 (50), 95 (9), 83 (40), 69 (19), 55 (26).

2. INVESTIGATIONS ON THE ANTIMICROBIAL EFFECT AGAINST BODY PERSPIRATION ODOR BACTERIA

The knowledge that the compound according to the invention is suitable for combating certain germs, which are responsible for the perspiration odor, goes back to series of investigations in which the particularly relevant germ *corynebacterium xerosis* and also *staphylococcus aureus* were investigated.

2.1 General Test Conditions:

The evidence of the antimicrobial action against body perspiration odor bacteria of the substances synthesized according to the examples was implemented with the aid of the agar dilution method according to DIN 58 940/ICS and DIN 58 944/ICS. Petri dishes of 5.5 cm in diameter were filled with 8.7 ml freshly produced Mueller-Hinton-agar or Wilkins-Chalgren-agar bouillon kept liquid at 50° C., supplemented with 10 g agar-agar/liter) to which the various concentrations of the thinned samples were added in 3.3% by volume=0.3 ml.

2.6 ml of the 3.3% samples were diluted with ethanol (96%). By continuous 2:1 dilution with ethanol (96%) the further test concentrations of the respective series of dilution, which were placed in the form of geometric rows, were produced.

By further dilution with the test agar (0.3 ml sample or corresponding dilutions+8.7 ml agar), 30 times lower end concentrations were achieved (corresponds to a starting concentration of 1,100 ppm in each case). The concentrations disclosed below relate to the pure substance and are converted into ppm. 2 agar plates were poured per test concentration and culture medium.

After solidification and drying (about 1 h at 37° C.), the test plates were inoculated point-wise with 1 µl in each case of the test germ suspensions listed in the following examples. To test purity and identity, the aerobically growing bacteria (*corynebacterium xerosis, staphylococcus aureus; staphylococcus epidermidis*) were cultivated on Colombia blood agar. The mould fungus *Aspergillus niger* was cultivated on Sabouraud agar. Further details on the test germs can be inferred from Table 1.

TABLE 1

Test germs (strain designations) and germ numbers

| Test Germ | Test designation | KBE*/ml |
|---|---|---|
| *Staphylococcus aureus* | ATCC 6538 | $1\text{-}6 \times 10^6$ |
| *Corynebacterium xerosis* | ATCC 7711 | $1.9 \times 10^7$ |
| *Aspergillus niger* | ATCC 16404 | $1.7 \times 10^7$ |

KBE*= colony-forming units

The production of the test germ suspensions of the aerobically growing bacteria germs took place by incubating Mueller-Hinton-bouillon at 36° C., which had been inoculated with a few individual colonies of the respective test germs. After achieving a significant clouding, an amount of sterile culture bouillon was added to the suspensions such that the clouding thereof corresponded to the McFarland Standard 0.5 (about $1.5 \times 10^8$ KBE/ml).

To produce the remaining test germ suspensions, the test strains were cultivated on the above-mentioned solid culture medium, harvested by means of sterile swabs and taken up or diluted in so much Mueller-Hinton-bouillon, that the clouding of the suspensions corresponded to the McFarland Standard 0.5.

All the test germ suspensions were diluted again with sterile bouillon 1:10 and the germ count thereof determined in the surface method per spiralometer (results: see Table 1).

The inoculated plates were incubated under the conditions given in Table 2 and then evaluated. The lowest active ingredient concentration was regarded as the MIC (minimal inhibition concentration), at which no growth is macroscopically present. Minimal, hardly visible growth or a few small individual colonies were evaluated as inhibition.

TABLE 2

Inoculation and incubation

| Test germ | Strain designation | Growth conditions | Culture medium | Incubation |
|---|---|---|---|---|
| *Staphylococcus aureus* | ATCC 6538 | Aerobic | Casein (soya peptone) | 18 h at 36° C. |
| *Corynebacterium xerosis* | ATCC 7711 | Aerobic | Mueller-Hinton-agar | 18 h at 36° C. |
| *Aspergillus niger* | ATCC 16404 | Aerobic | Mueller-Hinton-agar | 48 h at 30° C. |

2.2 MIC Value

The minimum inhibition concentration (MIC) of the compound according to the invention, was determined against various cosmetically relevant germs in the series dilution test (H. Brandis, G. Pulverer: Lehrbuch der Medizinischen Mikrobiologie, 6$^{th}$ revised edition, Gustav Fischer Verlag Stuttgart, 1988; page 200 et seq.). The test was transferred to the microtiter plate format and the concentration was determined as the MIC value, in which after 16 hours of incubation, at the wavelength of 620 nm, no significant rise in the clouding was observed relative to the controls.

The results are shown in Table 3.

TABLE 3

MIC values for L-menthyl-N-(2-hydroxyphenyl)carbamate

|  | MIC+ in [ppm] |
|---|---|
| *Corynebacterium xerosis* | 8 |
| *Staphylococcus aureus* | 8 |
| *Aspergillus niger* | >1000 |

A clear inhibition of the growth of gram-positive bacteria causing body odor perspiration such as *corynebacterium xerosis* could already be observed in very small concentrations. Relative to mould fungi such as *Aspergillus niger*, L-menthyl-N-(2-hydroxyphenyl)carbamate is inactive, on the other hand.

3rd Investigation of the Antioxidant Capacity of L-Menthyl-N-(2-hydroxyphenyl)carbamate with the Aid of ABTS Assays In order to check to what extent L-menthyl-N-(2-hydroxyphenyl)carbamate also has antioxidant potential, the substance was investigated with the aid of the ABTS assay. For the qualitative and quantitative evaluation of the antioxidant potential, the effectiveness thereof was compared with that of alpha-tocopherol, a highly active and versatile antioxidant.

Test Description for ABTS-Assay:

The ABTS assay is a cell-free in vitro test for evaluating the antioxidant capacity (literature: Re R, Pellegrini N, Proteggente A, Pannala A, Yang M, Rice-Evans C. 1999. "Antioxidant activity applying an improved ABTS radical cation decolorization assay"; Free Radic. Bio. Med. 26: 1231-7). The assay uses the inherent color of a solution produced with the cationic radical 2,2'-azinobis(3-ethylbenzothiazoline 6-sulfonic acid) (ABTS+) and potassium persulfate, which solution is decolored by the addition of antioxidants (reduction of the cationic radical). This decoloration can be measured photometrically at 734 nm.

The test is carried out in 96-well microtiter plates. The antioxidant capacity is expressed in $IC_{50}$ values (antioxidant concentration in which 50% of the cationic radicals are reduced). All the ABTS test results result from two independent tests and are shown as mean values with associated mean value deviation.

TABLE 4

Mean antioxidant capacity (AOX) of L-menthyl-N-(2-hydroxyphenyl)carbamate (L-MNC) and alpha-tocopherol

| Substance | Concentration [mM] | | | | | $IC_{50}$ [mM] |
|---|---|---|---|---|---|---|
|  | 0.001 | 0.0025 | 0.005 | 0.025 | 0.05 |  |
| Mean AOX L-MNC | 3.58 | 8.84 | 17.50 | 63.15 | 96.56 | 0.019 |
| Mean AOX alpha-tocopherol | 0.56 | 4.16 | 10.83 | 51.38 | 94.88 | 0.025 |

Result:

As the ABTS investigations show, the antioxidant capacity of L-menthyl-N-(2-hydroxyphenyl)carbamate is comparable with the antioxidant capacity of the reference substance alpha-tocopherol, from which it can be seen that L-menthyl-N-(2-hydroxyphenyl)carbamate, in addition to very good antimicrobial effectiveness against body perspiration odor bacteria, can also be excellently used as an antioxidant in cosmetic and pharmaceutical products.

3. FORMULATION EXAMPLES

Example 3.1

Water-in-Oil (W/O) Cream

|  | Weight % |
|---|---|
| Mineral oil | 10.00 |
| Ozocerite | 4.00 |
| Vaseline | 4.00 |
| Plant oil | 10.00 |
| Wool wax alcohol | 2.00 |
| Aluminum stearate | 0.40 |
| L-menthyl-N-(2-hydroxyphenyl)carbamate | 1.00 |
| Perfume, preservatives | q.s. |
| Water, VES | ad 100.00 |

Example 3.2

Oil-in-Water (O/W) Lotion

|  | Weight % |
|---|---|
| Mineral oil | 5.00 |
| Isopropyl palmitate | 5.00 |
| Cetyl alcohol | 2.00 |
| Beeswax | 2.00 |
| Ceteareth-20 | 2.00 |
| PEG-20-glycerylstearate | 1.50 |
| Glycerol | 3.00 |
| L-menthyl-N-(2-hydroxyphenyl)carbamate | 1.00 |
| Perfume, preservatives | q.s. |
| Water, VES | ad 100.00 |

Example 3.3

Shower Preparation with Moisturizers

|  | Weight % |
|---|---|
| Cocoamidodiacetate | 10.00 |
| Sodium lauryl sulfate | 25.00 |
| Potassium cocyl hydrolyzed collagen | 5.00 |
| Macadamia nut oil | 5.00 |
| Sodium chloride | 0.60 |
| L-menthyl-N-(2-hydroxyphenyl)carbamate | 0.30 |
| Perfume, preservatives | q.s. |
| Water | ad 100.00 |

Example 3.4

Piece of Soap

|  | Weight % |
| --- | --- |
| Na-salt of tallow fatty acids | 60.00 |
| Na-salt of coconut oil | 28.00 |
| Sodium chloride | 0.50 |
| L-menthyl-N-(2-hydroxyphenyl)carbamate | 1.20 |
| Perfume, preservatives | q.s. |
| Water | ad 100.00 |

Example 3.5

Syndet Soap

|  | Weight % |
| --- | --- |
| Sodium lauryl sulfate | 30.00 |
| Sodium sulfosuccinate | 10.00 |
| Potassium cocyl hydrolysed collagen | 2.00 |
| Dimethicone copolyol | 2.00 |
| Mineral oil | 2.00 |
| Maize starch | 10.00 |
| Talcum | 10.00 |
| Glycerol | 3.00 |
| L-menthyl-N-(2-hydroxyphenyl)carbamate | 1.00 |
| Perfume, preservatives | q.s. |
| Water | ad 100.00 |

Example 3.6

Hair Shampoo

|  | Weight % |
| --- | --- |
| Sodium lauryl sulfate | 34.00 |
| Disodium lauryl sulfosuccinate | 6.00 |
| Cocoamidopropyl betaine | 10.00 |
| Glycoldistearate | 5.00 |
| L-menthyl-N-(2-hydroxyphenyl)carbamate | 0.010 |
| Perfume, preservatives | q.s. |
| Water | ad 100.00 |

Example 3.7

Hair Conditioner

|  | Weight % |
| --- | --- |
| Cocoamidopropyl betaine | 5.00 |
| Cetyl alcohol | 2.00 |
| Propylene glycol | 2.00 |
| Citric acid | 0.30 |
| L-menthyl-N-(2-hydroxyphenyl)carbamate | 1.00 |
| Perfume, preservatives | q.s. |
| Water | ad 100.00 |

Example 3.8

Foot Cream

|  | Weight % |
| --- | --- |
| Soluan 5 | 2.00 |
| Methyl salicylate | 5.00 |
| Caprylic/capric triglyceride | 10.00 |
| Stearic acid | 5.00 |
| Cetyl alcohol | 1.00 |
| Glycerol | 2.00 |
| Dimethicone | 1.00 |
| Carbopol 984 | 0.50 |
| Triethanolamine | 1.50 |
| L-menthyl-N-(2-hydroxyphenyl)carbamate | 1.00 |
| Perfume, preservatives | q.s. |
| Water | ad 100.00 |

Example 3.9

Roll-on-Gel

|  | Weight % |
| --- | --- |
| 1,3-butylene glycol | 2.00 |
| PEG-40-hydrogenated castor oil | 2.00 |
| Hydroxyethylcellulose | 0.50 |
| L-menthyl-N-(2-hydroxyphenyl)carbamate | 0.30 |
| Perfume, preservatives | q.s. |
| Water | ad 100.00 |

Example 3.10

Deodorant Sticks

|  | Weight % | Weight % |
| --- | --- | --- |
| Sodium stearate | 7.00 | 8.00 |
| Sodium palmitate | 1.00 | — |
| 1,2-propylene glycol | Ad 100 | Ad 100 |
| 1,2-butylene glycol | 3.00 | — |
| 2-butyloctanoic acid | — | 0.50 |
| 2-hexyldecanoic acid | 0.30 | — |
| Polyethylene glycol(25)cetearylether | 3.00 | 3.00 |
| Ethanol | 20.00 | 20.00 |
| Parabens (mixture of methyl, ethyl, propyl, butyl, isobutylparaben) | 0.30 | — |
| 1,2-hexane diol/1,2-octane diol (1:1) | — | 0.60 |
| 1,2-pentane diol | 1.50 | — |
| (−)-alpha-bisabolol. nat. | 0.10 | — |
| L-menthyl-N-(2-hydroxyphenyl)carbamate | 0.55 | 0.85 |
| Perfume oil | 0.70 | 0.95 |

Example 3.11

Antiperspirant Sticks

| Component | Weight % | Weight % |
| --- | --- | --- |
| Phenyl trimethicone (SilCare TM Silicone 15 M 50) | 13.50 | 13.50 |
| Cetearyl alcohol | Ad 100 | Ad 100 |
| Cetiol CC (dicaprylyl carbonate) | 13.50 | 13.50 |

-continued

| Component | Weight % | Weight % |
|---|---|---|
| Stearic acid | 3.50 | 3.50 |
| PEG-40-hydrogenated castor oil (Emulsogen TM HCO 040) | 4.10 | 4.10 |
| PEG-8 distearate (Cithrol 4 DS) | 4.10 | 4.10 |
| Petrolatum | 6.90 | 6.90 |
| Aluminum chlorohydrate | 13.80 | 13.80 |
| Aluminum zirconium trichlorohydrex Gly | 20.00 | 19.50 |
| Neo Heliopan ® Hydro (phenylbenzimidazole sulfonic acid, Symrise) | 2.00 | — |
| Ethylhexylglycerol (octoxyglycerol) | — | 0.30 |
| L-menthyl-N-(2-hydroxyphenyl)carbamate | 0.65 | 0.95 |
| Perfume oil | 0.90 | 0.70 |

Example 3.12

Antiperspirant Formulations

| Component | Weight % | Weight % |
|---|---|---|
| Reach AZP-908 SUF (aluminum zirconium trichlorohydrex gly) | 24.00 | 22.00 |
| Cyclomethicone (pentamer) | Ad 100 | Ad 100 |
| Polydecene (Silkflo 364 NF) | 17.50 | 20.00 |
| Neo helipan OS (ethylhexyl salicylate, Symrise) | 2.50 | 1.00 |
| Polyethylene | 3.00 | 3.00 |
| Hydrogenated castor oil | 2.00 | 2.00 |
| Promyristyl PM-3 | 7.00 | 7.00 |
| PEG-8 distearate | 3.00 | 3.00 |
| Silicon dioxide (Cab-O-Sil M-5) | 1.00 | 1.00 |
| Stearyl alcohol | 15.00 | 10.00 |
| Octyldodecanol | — | 8.00 |
| L-menthyl-N-(2-hydroxyphenyl)carbamate | 0.65 | 0.95 |
| Perfume oil | 0.90 | 0.70 |

Example 3.13

Deodorant Aerosol Spray Based on Alcohol

| Component | Weight % | Weight % |
|---|---|---|
| Octyl dodecanol | — | 0.50 |
| 2-butyl decanoic acid | — | 0.45 |
| 2-hexyl decanoic acid | 0.50 | — |
| 1,2-pentane diol | 1.00 | 2.00 |
| 1,2-hexane diol | 0.25 | 0.20 |
| 1,2-octane diol | — | 0.20 |
| Farnesol | 0.15 | — |
| 2-methyl-5-phenylpentane-1-ol (rosaphene) | 0.10 | — |
| Ethylhexylglycerol (octoxyglycerol) | 0.25 | 0.50 |
| Phenoxyethanol | 0.25 | — |
| Perfume oil | 0.75 | 1.15 |
| L-menthyl-N-(2-hydroxyphenyl)carbamate | 0.50 | 0.75 |

The liquid mixture obtained after mixing together the respective disclosed components was filled with a propane-butane mixture (quantity ratio 2:7) in the ratio 2:3 into an aerosol container.

Example 3.14

Antiperspirant Spray 40 parts by weight of aluminum chlorohydrate are added to a mixture of suitable carrier substances consisting of 12.5 parts by weight miglyol 840 gel B (mixture of propylene glycol dicaprylate/dicaprate, steralconium hectorite and propylene carbonate; Producer: Sasol), and 46.5 parts by weight silicone oils (cyclomethicone, dimethiconol; Producer: Dow Corning). When the mixture has become homogeneous, 1.5 parts by weight of perfume oil and 1 part by weight of L-menthyl-N-(2-hydroxyphenyl)carbamate are added. An aerosol spray, which was used as an antiperspirant spray on numerous test subjects to combat armpit perspiration odor, was produced from 1 part by weight of the resulting solution and 3 parts by weight of a propellant (propane/butane; pressure 2.5 to 2.7 bar).

The invention claimed is:

1. A preparation for treating body odor comprising an antimicrobial amount of L-menthyl-N-(2-hydroxyphenyl)carbamate:

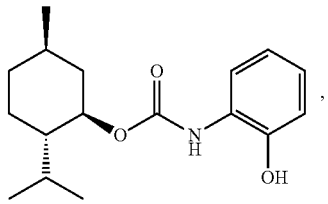 [SMILES: CC(C)[C@@H]1CC[C@@H](C)C[C@H]1OC(=O)Nc1ccccc1O]

and a compatible carrier,
provided that the concentration of the L-menthyl-N-(2-hydroxyphenyl)carbamate is from 0.001 to 20% by weight, based on the total weight of the preparation.

2. The preparation as claimed in claim 1, further comprising one or more additional antimicrobially effective substances, enzyme-inhibiting substances, odor-absorbing substances, and/or antiperspirants.

3. The preparation as claimed in claim 1, wherein the preparation is a pharmaceutical preparation or a cosmetic preparation.

4. The preparation as claimed in claim 1, wherein the L-menthyl-N-(2-hydroxyphenyl)carbamate is in a concentration of 0.05 to 5% by weight, based on the total preparation.

5. The preparation as claimed in claim 4, wherein the L-menthyl-N-(2-hydroxyphenyl)carbamate is in a concentration of 0.1 to 3% by weight, based on the total preparation.

6. The preparation as claimed in claim 1 in the form of a deodorant, antiperspirant, or shampoo.

7. A topical application device for the human body comprising a preparation as claimed in claim 1.

8. A method for treating body odor comprising applying the preparation according to claim 1 to the body and killing or preventing the proliferation of odor causing bacteria, thereby treating body odor.

9. The method of claim 8, wherein the bacteria are selected from the group consisting of staphylococcus, corynebacterium, and brevibacterium.

10. The method of claim 8, wherein the preparation is applied to the armpit.

11. An anti-oxidant effective cosmetic or pharmaceutical preparation comprising the preparation according to claim 1.

12. A method of improving resistance of a cosmetic or pharmaceutical preparation against oxidation comprising incorporating the preparation according to claim 1 into the cosmetic or pharmaceutical preparation.

* * * * *